US008540658B2

(12) United States Patent
Stoll

(10) Patent No.: US 8,540,658 B2
(45) Date of Patent: Sep. 24, 2013

(54) BONE-REGENERATION MATERIAL

(75) Inventor: Thierry Stoll, Sutz (CH)

(73) Assignee: DePuy Synthes Products, LLC, Raynham, MA (US)

(*) Notice: Subject to any disclaimer, the term of this patent is extended or adjusted under 35 U.S.C. 154(b) by 740 days.

(21) Appl. No.: 10/370,606

(22) Filed: Feb. 24, 2003

(65) Prior Publication Data

US 2005/0074433 A1 Apr. 7, 2005

Related U.S. Application Data

(63) Continuation of application No. PCT/CH01/00494, filed on Aug. 13, 2001.

(51) Int. Cl.
*A61M 31/00* (2006.01)

(52) U.S. Cl.
USPC .......................... 604/6.12; 424/423

(58) Field of Classification Search
None
See application file for complete search history.

(56) References Cited

U.S. PATENT DOCUMENTS

| | | | |
|---|---|---|---|
| 2,337,149 A | 12/1943 | Bullock | |
| 4,529,511 A | 7/1985 | Breeden et al. | |
| 4,758,096 A | 7/1988 | Gunnarsson | |
| 4,808,184 A | 2/1989 | Tepic | |
| 4,842,581 A | 6/1989 | Davis | |
| 5,051,482 A | 9/1991 | Tepic | |
| 5,139,031 A * | 8/1992 | Guirguis | 600/584 |
| 5,164,186 A | 11/1992 | Tsuru et al. | |
| 5,181,918 A | 1/1993 | Brandhorst et al. | |
| 5,344,417 A | 9/1994 | Wadsworth, Jr. | |
| 5,425,770 A * | 6/1995 | Piez et al. | 424/423 |
| 5,496,284 A | 3/1996 | Waldenburg | |
| 5,529,463 A | 6/1996 | Layer et al. | |
| 5,531,255 A | 7/1996 | Vacca | |
| 5,549,380 A | 8/1996 | Lidgren | |
| 5,711,957 A | 1/1998 | Patat et al. | |
| 5,755,787 A | 5/1998 | Camprasse et al. | |
| 5,772,665 A * | 6/1998 | Glad et al. | 604/82 |
| 5,842,786 A | 12/1998 | Solomon | |
| 5,846,484 A | 12/1998 | Scarborough | |
| 5,876,452 A * | 3/1999 | Athanasiou et al. | 623/23.72 |
| 6,027,742 A | 2/2000 | Lee et al. | |
| 6,049,026 A * | 4/2000 | Muschler | 424/93.7 |
| 6,123,236 A | 9/2000 | Bloom | |
| 6,143,293 A * | 11/2000 | Weiss et al. | 424/93.7 |
| 6,383,190 B1 | 5/2002 | Preissman | |
| 6,409,708 B1 * | 6/2002 | Wessman | 604/284 |
| 6,682,347 B2 | 1/2004 | Aoyagi et al. | |
| 6,709,149 B1 | 3/2004 | Tepic | |
| 6,736,799 B1 * | 5/2004 | Erbe et al. | 604/181 |
| 6,796,957 B2 | 9/2004 | Carpenter et al. | |
| 6,887,272 B2 | 5/2005 | Shinomiya et al. | |
| 7,445,633 B2 | 11/2008 | Hoerger et al. | |
| 2004/0226894 A1 | 11/2004 | Okazaki | |
| 2004/0254538 A1 | 12/2004 | Murphy et al. | |
| 2004/0267201 A1 | 12/2004 | Agerup | |
| 2005/0074433 A1 | 4/2005 | Stoll | |
| 2006/0153001 A1 | 7/2006 | Hoerger et al. | |
| 2007/0221742 A1 | 9/2007 | Hoerger et al. | |
| 2008/0214998 A1 | 9/2008 | Kurek et al. | |
| 2009/0022878 A1 | 1/2009 | Hoerger | |

FOREIGN PATENT DOCUMENTS

| | | |
|---|---|---|
| CA | 1260391 | 3/1986 |
| CA | 2419850AA | 2/2002 |
| CN | 1251046 | 4/2000 |
| DE | 3834944 | 4/1990 |
| DE | 4141129 | 6/1993 |
| EP | 0361896 A2 | 4/1990 |
| EP | 0361896 A3 | 1/1991 |
| EP | 0470393 A1 | 2/1992 |
| EP | 0739631 A2 | 10/1996 |
| EP | 0761896 A1 | 3/1997 |
| EP | 1230942 A2 | 8/2002 |
| FR | 2815021 A1 | 4/2002 |
| JP | 60-142857 | 7/1985 |
| JP | 61226055 | 10/1986 |
| JP | S61226055 A | 10/1986 |
| JP | 03-085179 | 4/1991 |
| JP | H04244164 | 1/1992 |
| JP | 4244164 | 2/1992 |
| JP | 5305134 | 4/1992 |
| JP | 04-221538 | 8/1992 |
| JP | H05305134 | 11/1993 |
| JP | 07-008547 | 1/1995 |
| JP | 07-313586 | 12/1995 |
| JP | 08-024347 | 1/1996 |

(Continued)

OTHER PUBLICATIONS

Medline Plus medical dictionary definition of "osteogenic." Accessed online Dec. 12, 2005. 1 page.*
Dictionary.com definition of "mesenchymal." Accessed online Dec. 12, 2005. 1 page.*
EPOline Online Public File Inspection entry for WIPO document WO2000CH00443. Accessed online Dec. 13, 2005. 1 page.*
Linkhart TA et al. 1996. Growth factors for bone growth and repair: IGF; TGF beta, and BMP. Bone 19 (1 Suppl):1S-12S. Abstract only. 1 page.*
"Body." in: Costello, RB, ed., Random House Webster's College Dictionary (1991 ed.), p. 152.*
Definition of "membrane." The American Heritage® Dictionary of the English Language, Fourth Edition Copyright © 2007, 2000 by Houghton Mifflin Company. Updated in 2007. 2 pages.*
Merriam-Webster MedLine Plus Online Medical Dictionary definitions of "vacuum," "membrane," and "septum." Accessed online at <http://www.nlm.nih.gov/medlineplus/mplusdictionary.html> on Oct. 16, 2008.*

(Continued)

*Primary Examiner* — Lora E. Barnhart Driscoll

(74) *Attorney, Agent, or Firm* — Morgan Lewis & Bockius LLP.

(57) ABSTRACT

The invention relates to a process for producing a bone-regeneration material. According to the method, a bio-compatible, open-pored body is exposed to a vacuum and osteoinductive and/or osteogenic substances are absorbed into the pores of the body, for example by means of a vacuum generated therein. It is thus possible to produce a bone-regeneration material, which contains osteoinductive and/or osteogenic substances in the pores of the bio-compatible body, said substances acting as a network structure for new somatic cells that are to grow into the porous body.

19 Claims, 1 Drawing Sheet

(56) References Cited

FOREIGN PATENT DOCUMENTS

| | | |
|---|---|---|
| JP | 1996503157 | 4/1996 |
| JP | H08503157 A | 4/1996 |
| JP | 09-201330 | 8/1997 |
| JP | 2000508911 | 7/2000 |
| JP | 2000508911 A | 7/2000 |
| JP | 2001137328 | 5/2001 |
| JP | 2001137328 A | 5/2001 |
| JP | 2003010301 | 1/2003 |
| WO | 9740137 | 10/1997 |
| WO | WO-9746202 A1 | 12/1997 |
| WO | 9959500 | 11/1999 |
| WO | WO-00/45867 A1 | 8/2000 |
| WO | WO-01/32100 A2 | 5/2001 |
| WO | WO-0215950 A1 | 2/2002 |
| WO | WO-02068010 A1 | 9/2002 |
| WO | WO-2005014068 A1 | 2/2005 |

OTHER PUBLICATIONS

"U.S. Appl. No. 11/349,693, Non-Final Office Action Mailed Sep. 7, 2007", 9.

"U.S. Appl. No. 11/349,693 response filed Dec. 7, 2007 to Office Action mailed Sep. 7, 2007.", 10 pgs.

International Search Report for Application No. PCT/CH03/00537, date mailed Apr. 16, 2004, 3 pgs.

"U.S. Appl. No. 11/349,693, Response filed Jun. 16, 2008 to Final Office Action mailed Mar. 17, 2008", 8 pgs.

"U.S. Appl. No. 11/349,693 Notice of Allowance mailed Jun. 30, 2008", NOAR,5 pgs.

"U.S. Appl. No. 11/349,693 Final Office Action mailed Mar. 17, 2008", FOAR,12 Pgs.

"European Patent Application No. 04750971.6, Communication mailed Jun. 12, 2008", 5 pgs.

"International Patent Application Serial No. PCT/CH01/00494, International Preliminary Examination Report dated Aug. 26, 2002", (w/ English Translation), 15 pgs.

"International Patent Application Serial No. PCT/CH01/00494, International Search Report mailed Dec. 5, 2001", (w/ English Translation), 8 pgs.

"Japanese Application No. 2002-506661, Notice of the Reason for the Rejection mailed Feb. 27, 2008", (w/ English Translation), 7 pgs.

"Japanese Application No. 2002-506661, Official Notice of Reason for the Final Rejection mailed Jul. 11, 2008", (w/ English Translation), 4 pgs.

Kaneko, Y., et al., "Synthesis and Swelling—deswelling kinetics of poly(N-isopropylacrylamide) hydrogels grafted with LCST modulated polymers", *Journal of Biomaterials Science, Polymer Edition*, 10(11), (1999), 1079-1091.

Stile, R. A., et al., "Synthesis and Characterization of Injectable Poly(N-isopropylacrylamide)-Based Hydrogels That Support Tissue Formation in Vitro", *Macromolecules*, 32, (1999), 7370-7379.

"U.S. Appl. No. 12/242,207, Final Office Action mailed May 4, 2009", 9 pgs.

"Canada Application Serial No. 2,419,850, Office Action mailed Jul. 7, 2009", 3 pgs.

"U.S. Appl. No. 12/242,207, Response filed Nov. 3, 2009 to Non Final Office Action mailed May 4, 2009", 7 pgs.

International Application Serial No. PCT/US06/41202, International Preliminary Report on Patentability mailed Sep. 3, 2008.

International Application Serial No. PCT/US06/41202, International Search Report mailed Sep. 26, 2007.

International Application Serial No. PCT/US06/41202, Written Opinion mailed Sep. 26, 2007.

Barry T. Mitzner, Hematology Methods for the Office Laboratory Power Point Presentation, Jun. 12, 1999.

European Patent Application No. 04750971.6, Communication mailed Jun. 12, 2008.

Definition of "Osteogenic", Medline Plus®, [online]. © 2005 Merriam-Webster, Incorporated. [retrieved Dec. 12, 2005]. Retrieved from the Internet: <URL: http://ww2.merriam-webster.com/cgi-bin/mwmednlm?book=Medical&va=osteogenic>.

U.S. Appl. No. 12/089,679, Non-Final Office Action mailed Dec. 24, 2009.

U.S. Appl. No. 12/089,679, Final Office Action mailed Jul. 13, 2010.

"International Application Serial No. PCT/CH2004/000335", Written Opinion mailed Feb. 9, 2005, (with English translation), 10 pages.

"International Application Serial No. PCT/CH2004/000335", International Search Report mailed Feb. 9, 2005, (with English translation), 6 pages.

Notice of Reasons for Rejection for Japanese Patent Application No. 2002-520871 dated Sep. 16, 2011.

Taiwan patent application No. 94113414, English Translation of an Office action dated Jul. 22, 2011 (5 pages).

Taiwan patent application No. 94113414, Taiwanese version of the Office action dated Jul. 22, 2011 (12 pages).

Japanese Office Action dated Sep. 13, 2011 from corresponding Japanese Application No. 2002-520871 with English Translation.

\* cited by examiner

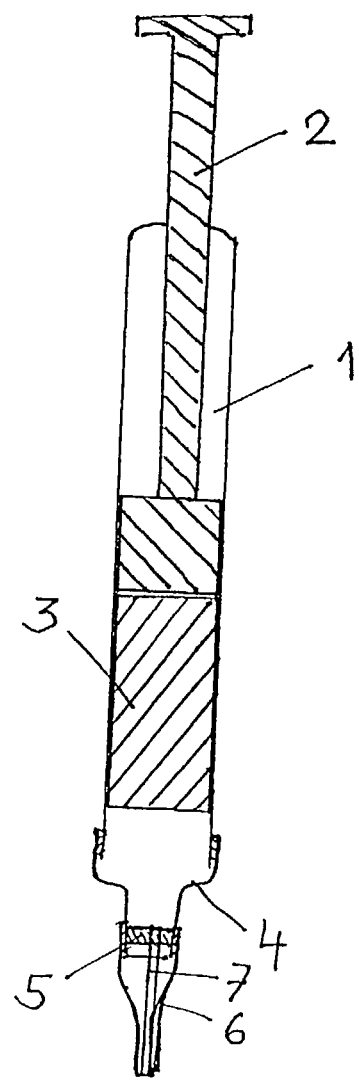

BONE-REGENERATION MATERIAL

CROSS-REFERENCE TO RELATED APPLICATIONS

This application is a continuation of the International Patent Application No. PCT/CH01/00494, filed Aug. 13, 2001, which claims the benefit of International Patent Application PCT/CH00/00443, filed Aug. 22, 2000, the entire contents of which are expressly incorporated herein by reference thereto.

FIELD OF THE INVENTION

The present invention relates generally to a process for the production of a bone replacement material, an apparatus for carrying out this process according, and a bone replacement material.

BACKGROUND OF THE INVENTION

Japanese patent application No. 60 142857 discloses a porous hydroxyapatite body which can contain water, aqueous sodium chloride solution, blood, and artificial blood plasma.

PCT/EP99/00684 discloses bone replacement materials which are biocompatible and osteoconductive. Osteoconduction is defined as growth of osteoblasts and bone regeneration, free of intermediate layers, on the surface of the body's own material or of introduced foreign material without their experiencing a change under bone growth.

The absence of osteoconduction is disadvantageous in these known materials. Osteoconduction is understood to mean an intervention, non-physiological in principle, into the tissue distribution of the body. Osteoinduction means initiating and stimulating bone growth in a region of tissue which contains bone tissue, in this connection the open-pore structure of a biomaterial.

A need exists for a simple and reliable process for the production of a bone material, in particular with an improved osteoinductivity.

SUMMARY OF THE INVENTION

The present invention is directed to a process for the production of a bone regeneration material which contains at least one of: an osteoinductive substance and an osteogenic substance. The process comprises providing a biocompatible, open-pore body, exposing the pores of the biocompatible, open-pore body to a vacuum, and drawing the at least one substance into the pores.

In a preferred process the osteogenic substance comprises somatic cells chosen from the group consisting of: autologous bone marrow, separated, concentrated cells from autologous bone marrow, cultivated autologous stem cells, differentiated autologous stem cells, and mesenchymal cells. In one embodiment, the osteoinductive substance is contained in a body-compatible liquid, such as an aqueous solution. In another embodiment, the osteogenic substance is suspended in a body-compatible liquid. In another preferred embodiment, the somatic cells are of an autologous nature.

In another preferred embodiment of the invention, substances promoting bone growth are mixed, in flowable form, with the somatic cells such as, for example, a) synthetic growth factors, b) recombinant growth factors, preferably β growth factor (TGF-β) or FGF-2 (fibroblast growth factor), c) natural or synthetic peptides, d) platelet-derived growth factor (PDGF), e) insulin-like growth factor (IGF), f) fibrin as end product of blood coagulation, and g) synthetic fibrin.

In one preferred embodiment, the process is performed in a syringe with a hollow cylinder and a piston, and the osteoinductive and/or osteogenic substances in flowable form are drawn into the syringe and drawn through the pores of the body housed in the hollow cylinder.

The present invention is also directed to an apparatus for carrying out the process according to claim a syringe with a hollow cylinder and a piston, and a biocompatible, open-pore body is housed in the hollow cylinder, said body obstructing a portion of the hollow cylinder so that at least one of the osteoinductive substance or osteogenic substance flows through the pores of the body when it is drawn by the syringe.

In one preferred embodiment, the syringe has a head part, which is fastenable on the front end of the hollow cylinder, with a membrane so that at least one of the osteoinductive substance or osteogenic substance is drawn by the syringe, after sealing of the membrane and withdrawal of the piston, and flows through the pores of the body by means of a vacuum.

The invention is also directed to a bone regeneration material, comprising a biocompatible, open-pore body, wherein at least a part of the pores of the body is filled with at least one of: somatic cells or osteoinductive substances that are not blood based. In one embodiment, the body consists at least partially of a bioresorbing material. In another embodiment, the bioresorbing material comprises hydroxylapatite. In yet another embodiment, the bioresorbing material comprises tricalcium phosphate. In one embodiment, the porosity of this body is at least 25%, and in another embodiment the porosity is at least 35%. In another embodiment, at least 50% of the pores have a diameter in the range of 200 to 500 microns. In yet another embodiment, the connections between the individual pores have a diameter in the range of 10 to 300 microns, and in another embodiment in the range of 200 to 400 microns.

BRIEF DESCRIPTION OF THE DRAWINGS

Preferred features of the present invention are disclosed in the accompanying drawings, wherein similar reference characters denote similar elements throughout the several views, and wherein:

FIG. 1 is a cross-sectional view of an apparatus for use in the process according to the invention.

DETAILED DESCRIPTION OF THE PREFERRED EMBODIMENTS

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto.

FIG. 1 shows a preferred embodiment of an apparatus for the production of the bone replacement material according to the invention. Generally, the apparatus comprises a hollow cylinder 1, a piston 2 movably disposed in the hollow cylinder, and a head part 4 which can be screwed on the front end of the hollow cylinder 1. Head part 4 has a membrane 5 which is perforated by means of an adapter 6 with a perforating needle 7, and is generally used for withdrawing blood. With use of the adapter 6 on the head part 4, the adaptation of a standard cannula system (for example, Luer system—injection needle, catheter, butterfly, etc.) to the syringe becomes possible.

A biocompatible, open-pore body 3 is housed in hollow cylinder 1, and seals or obstructs the hollow cylinder 1 in the front section of the syringe so that a patient's blood or blood components sucked or drawn up by the syringe must flow through the body 3. Generally, the bio-compatible body 3 comprises a bioresorbing material. For example, in one preferred embodiment body 3 comprises a hydroxylapatite, and in another embodiment body 3 comprises a tricalcium phosphate. The porosity of body 3 is preferably at least 25%, more preferably at least 35%. Preferably, at least 50% of the pores have a diameter in the range of 200 to 500 microns. The connections between the individual pores may have a diameter in the range of 10 to 300 microns, preferably from 200 to 400 microns.

After withdrawing the blood, the adapter 6 is removed. Thus, the membrane 5 of the head part 4 is sealed once more and the contents of the hollow cylinder 1 of the syringe are once again sealed air-tight. Due to the vacuum arising on further drawing back of the piston 2 in the hollow cylinder 1 of the syringe, the blood flows through the entire body 3, penetrates up to its center, and expels the air contained therein. Instead of blood or blood components (or growth factors promoting bone formation), which are flowable as is, somatic cells can also be suspended in a body-compatible liquid, such as in an aqueous solution, in order to suck or draw them into the pores of the open-pore body.

After successful impregnation of the body 3 with blood or blood components (or other somatic cells in the flowable state), the head part 4 can be screwed off of the syringe so that the impregnated body 3 can be pushed out of the hollow cylinder 1 by means of the piston 2. The body 3 can then, if necessary after successful adaptation of its external form, be inserted in a prepared hole, or a bone defect, in the bone of the patient from whom the blood or other somatic cells needed for impregnation were drawn. Due to the open-porosity of the body 3 and the autologous blood (or blood components or other somatic cells) located in the pore system, the growth of somatic cells in the body 3 is strongly promoted.

In one preferred embodiment, the somatic cells are chosen from the group consisting of: autologous bone marrow, separated, concentrated cells from autologous bone marrow, cultivated autologous stem cells, differentiated autologous stem cells, or mesenchymal cells. The precursor cells (precursors) of the cells of the peripheral blood are constantly reproduced from immature hematopoetic cells, the so-called stem cells. Advantageously the somatic cells are of an autologous nature, that is, the donor and the recipient of the somatic cells are the same individual.

In one preferred embodiment of the invention, substances promoting bone growth are mixed, in flowable form, with the somatic cells such as, for example, a) synthetic growth factors, b) recombinant growth factors, preferably β growth factor (TGF-β) or FGF-2 (fibroblast growth factor), c) natural or synthetic peptides, d) platelet-derived growth factor (PDGF), e) insulin-like growth factor (IGF), f) fibrin as end product of blood coagulation, or g) synthetic fibrin.

It will be appreciated, that when the somatic cells are located in the pores of the biocompatible body (for example, blood or the fibrin contained therein) a network structure is formed for the somatic cells to be newly grown in the porous body. With the use of blood, the growth of the bone cells in the porous body is further promoted by the growth factors present in the blood platelets. An advantage of the process according to the invention consists of the fact that the porous body is not simply immersed in a suspension of somatic cells (for example, blood), in order to fill it by the capillary action of the pore system, but rather a vacuum is actively generated in the pores connected to one another by means of which osteoinductive and/or osteogenic substances in the flowable state (for example, in the form of blood or in the form of an aqueous suspension) can be sucked in homogeneously and up to the innermost part of the porous body.

It will be appreciated that when the bone replacement material produced according to the invention, with its open-pore structure filled with suitable somatic cells, e.g. blood, blood components (or growth factors promoting bone formation), bone marrow, or bone cells (all in a flowable form suitable for this purpose) and implanted in a defect, it possesses beneficial osteoinductive properties. The blood clot in the interior of the structure organizes itself better, similar to healing of a fracture, into a granular, low-fiber, connective tissue rich in cells and vessels: the granulation tissue. Diverse cells migrate into it and start the buildup of a cartilaginous matrix. This process continues until the entire granulation tissue is replaced by cartilage and later calcifies. Without such advantages, this entire biological process would slowed down or made impossible by the pores filled only with air.

While various descriptions of the present invention are described above, it should be understood that the various features can be used singularly or in any combination thereof. Therefore, this invention is not to be limited to only the specifically preferred embodiments depicted herein. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

The invention claimed is:

1. A process for the production of a bone regeneration material which contains a drawable substance that includes (i) at least one osteoinductive substance, (ii) at least one osteogenic substance, or (iii) at least one osteoinductive substance and at least one osteogenic substance, the process being performed with a syringe with a hollow cylinder, a piston, and an air tight seal and comprising:
   (a) housing a biocompatible, interconnected open-pore body in the hollow cylinder of the syringe;
   (b) forming a perforation in the air tight seal;
   (c) drawing the drawable substance through the perforation;
   (d) after drawing the drawable substance through the perforation, sealing the perforation; and
   (e) after sealing the perforation, drawing the drawable substance into pores of the biocompatible, interconnected open-pore body by further displacing the piston to create negative pressure within the hollow cylinder of the syringe.

2. The process according to claim 1, wherein the osteogenic substance is somatic cells in blood or an aqueous suspension, and the somatic cells are chosen from the group consisting of:
   (a) autologous bone marrow,
   (b) separated, concentrated cells from autologous bone marrow,
   (c) cultivated autologous stem cells,
   (d) differentiated autologous stem cells, and
   (e) mesenchymal cells.

3. The process according to claim 1, wherein the osteoinductive substance is contained in a body-compatible liquid.

4. The process according to claim 1, wherein the osteogenic substance is suspended in an aqueous solution.

5. The process according to claim 1, wherein the osteogenic substance is present in the form of somatic cells in flowable form, and the somatic cells are chosen from the group consisting of:
(a) blood,
(b) blood components,
(c) bone marrow, and
(d) bone cells.

6. The process according to claim 1, wherein the osteogenic substance is somatic cells of an autologous nature.

7. The process according to claim 1, wherein the osteoinductive substance is chosen from the group consisting of:
(a) synthetic growth factors,
(b) recombinant growth factors,
(c) β growth factor (TGF-β),
(d) FGF-2 (fibroblast growth factor),
(e) natural or synthetic peptides,
(f) platelet-derived growth factor (PDGF),
(g) insulin-like growth factor (IGF),
(h) fibrin as end product of blood coagulation, and
(i) synthetic fibrin.

8. A method, comprising:
placing a biocompatible open-pore body in a chamber of a syringe;
drawing at least one flowable substance into the chamber through a needle inserted through a membrane;
removing the needle from the membrane to form an air tight seal; and
after sealing the membrane, continuing to draw a syringe piston to produce a level of vacuum that is maintained within the chamber to draw the flowable substance into pores of the biocompatible open-pore body.

9. The method of claim 8, wherein the needle is in a removable adapter.

10. The method of claim 9, wherein the removable adapter is configured to couple to a cannula system chosen from a group consisting of a hub connection system, an injection needle, a catheter, and a butterfly.

11. The method of claim 10, wherein a removable head part including the membrane is coupled between the chamber and the removable adapter.

12. The method of claim 11, further including removing the removable head part after drawing the flowable substance into pores of the biocompatible open-pore body to provide an exit pathway, and expelling the biocompatible open-pore body through the exit pathway.

13. The method of claim 1 wherein step (f) further comprises expelling air from the biocompatible, interconnected open-pore body.

14. A method, comprising:
placing a biocompatible resorbable open-pore body in a chamber of a hollow cylinder;
coupling a membrane to said hollow cylinder to form an airtight seal;
inserting a cannula through said membrane;
drawing a flowable substance into the chamber through the cannula;
removing the cannula from the membrane to reform the air tight seal; and
after removing the cannula from the membrane to reform the air tight seal, producing and maintaining a level of vacuum within the chamber to draw the at least one flowable substance into pores of the biocompatible resorbable open-pore body and expel air from the biocompatible open-pre body as the flowable substance is drawn into the biocompatible resorbable open-pore body.

15. The method of claim 14, wherein coupling the membrane to the hollow cylinder includes attaching a head part to the hollow cylinder, said head part including the membrane.

16. The method of claim 15, wherein the head part has a first portion engageable with the hollow cylinder and a second portion engageable with an adapter, wherein the first portion of the head part has a diameter larger than a diameter of the second portion of the head part.

17. The method of claim 15, wherein inserting the cannula through the membrane includes attaching an adapter to the head part, the adapter including the cannula.

18. The method of claim 17, wherein the adapter has a first portion engageable with the head part and a second portion engageable with a Luer system, wherein the first portion of the adapter has a diameter larger than a diameter of the second portion of the adapter.

19. The method of claim 18, wherein the Luer system includes one or more of an injection needle, a catheter and a butterfly needle.

* * * * *